United States Patent [19]
Payne et al.

[11] Patent Number: 4,863,023
[45] Date of Patent: Sep. 5, 1989

[54] SHIPPING AND STORAGE CONTAINER FOR SYRINGES

[75] Inventors: John B. Payne, West Des Moines, Iowa; David R. Jones, West Palm Beach, Fla.

[73] Assignee: Diamond Scientific Company, Des Moines, Iowa

[21] Appl. No.: 212,683

[22] Filed: Jun. 20, 1988

[51] Int. Cl.⁴ ............................................. B65D 81/06
[52] U.S. Cl. ................................ 206/364; 206/45.34; 206/523
[58] Field of Search .............. 206/366, 588, 589, 592, 206/523, 45.34, 364, 379, 590; 220/306

[56] References Cited

U.S. PATENT DOCUMENTS

| 759,588 | 5/1904 | Baird | 206/366 |
|---|---|---|---|
| 2,774,472 | 12/1956 | Badalich | 220/306 X |
| 4,235,338 | 11/1980 | Dugan et al. | 206/528 |
| 4,503,972 | 3/1985 | Nelligan et al. | 206/588 X |
| 4,657,138 | 4/1987 | Watson | 206/366 |
| 4,742,934 | 5/1988 | Michaud et al. | 220/306 |
| 4,747,510 | 5/1988 | Mack | 220/306 X |
| 4,776,459 | 10/1988 | Beckerman et al. | 206/45.34 |

FOREIGN PATENT DOCUMENTS

| 818956 | 6/1937 | France | 206/366 |
|---|---|---|---|
| 2375109 | 8/1978 | France | 206/45.34 |
| 1539870 | 2/1979 | United Kingdom | 206/45.34 |
| 2173174 | 10/1986 | United Kingdom | 206/523 |

Primary Examiner—William Price
Attorney, Agent, or Firm—Zarley McKee, Thomte, Voorhees & Sease

[57] ABSTRACT

The container of the present invention for storing and shipping syringes comprises a base with a plurality of ports, each adapted to receive a syringe, and a cover which fits over the syringes and locks onto the base. The base is made of insulative material so as to protect the medicinal fluid within the syringes from temperature extremes. The cover is transparent for easy identification of the contents. The sidewalls of the cover are corrugated to provide strength to the cover. The top of the cover and the bottom of the base are flat so that a plurality of containers can be stacked one upon another for shipping and storage.

16 Claims, 1 Drawing Sheet

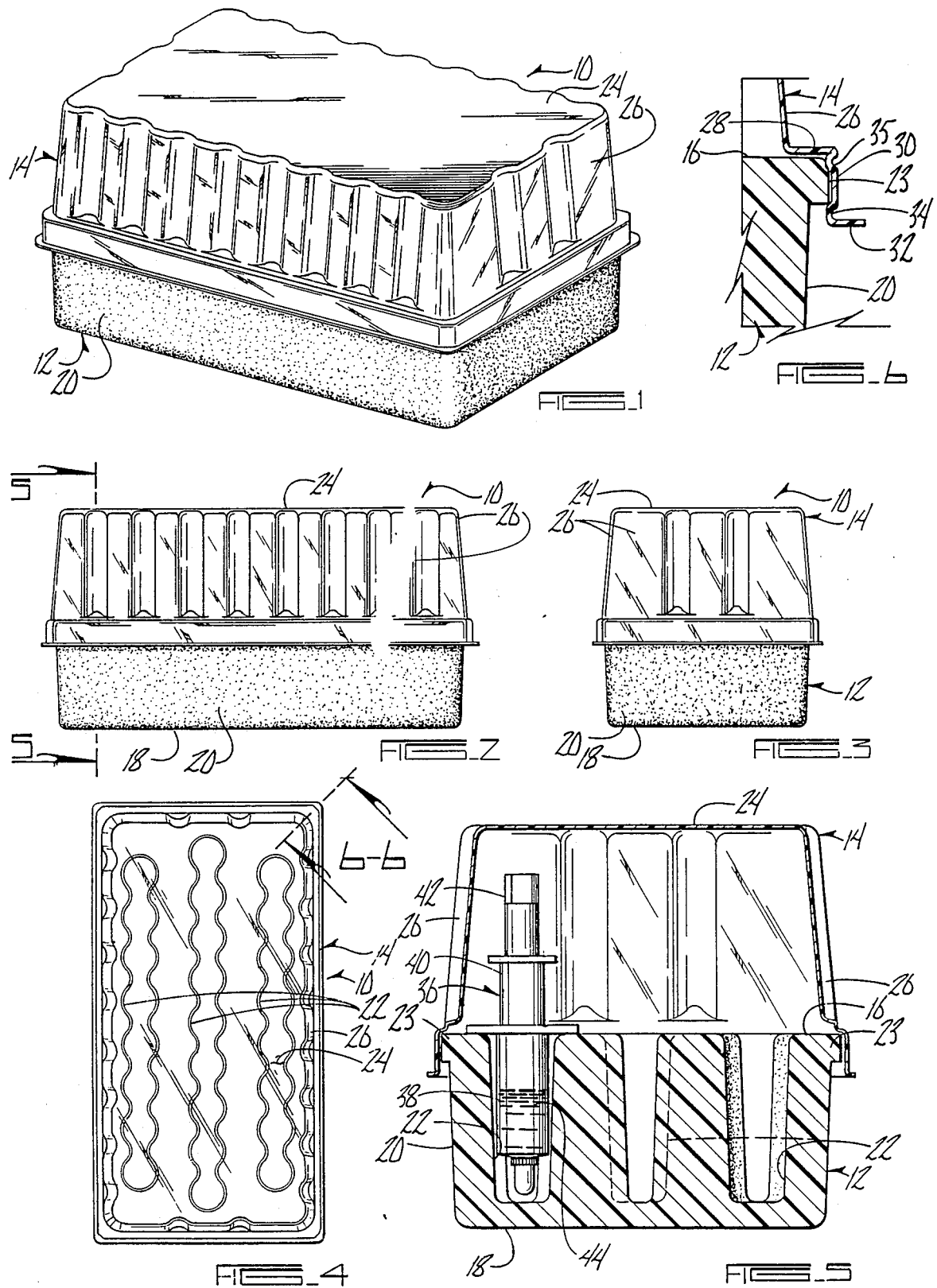

SHIPPING AND STORAGE CONTAINER FOR SYRINGES

BACKGROUND OF THE INVENTION

Syringes are often pre-filled with the fluid to be injected prior to shipping and storing of the filled syringes. Such pre-filled syringes must be protected from temperature extremes to avoid damage to the medicinal fluid. Also, it is desirable to protect the pre-filled syringes from physical damage during shipping and storage.

Accordingly, a primary objective of the present invention is the provision of an improved shipping and storage container for syringes.

Another objective of the present invention is the provision of a syringe container which protects the fluid within the syringes from temperature extremes.

A further objective of the present invention is the provision of a syringe container which allows for easy identification of the contents.

Still another objective of the present invention is the provision of a shipping and storage container for syringes which is economical to manufacture and durable in use.

SUMMARY OF THE INVENTION

The syringe container of the present invention includes a base having a plurality of holes or ports extending downwardly therein, with each port being adapted to receive a syringe. A cover fits over the syringes and locks onto the base to provide an enclosed container. The base is made of an insulative material, such as styrofoam, so as to protect the syringe from temperature extremes. The cover is transparent so as to allow easy identification of the syringes. Also, the top and bottom of the container is flat so that multiple containers can be stacked one on top of another.

BRIEF DESCRIPTION OF THE DRAWINGS

FIG. 1 is a perspective view of the syringe container of the present invention.

FIG. 2 is a side elevational view of the container.

FIG. 3 is an end elevational view of the container.

FIG. 4 is a top plane view of the container.

FIG. 5 is a sectional view taken along lines 5—5 of FIG. 2.

FIG. 6 is an enlarged partial sectional view taken along lines 6—6 of FIG. 4.

DETAILED DESCRIPTION OF THE DRAWINGS

The syringe container of the present invention is generally designated by the reference numeral 10 in the drawings. Container 10 includes a base 12 and a cover 14.

Base 12 includes a top surface 16, a flat bottom surface 18, and interconnected side walls 20. A plurality of ports or holes 22 extend downwardly from top surface 16 and terminate within base 12. Each port 22 is adapted to receive a syringe, as seen in FIG. 5. Base 12 also includes an outwardly projecting lip 23 which extends around the sidewalls 20 adjacent top 16.

Cover 14 includes a flat top 24 and interconnected sidewalls 26. The bottom of the cover is open so that the cover can fit over the syringes, as seen in FIG. 5. Sidewalls 26 are corrugated so as to provide strength for the cover. Sidewalls 26 of cover 14 terminate in an outwardly projecting lip 28, a downwardly extending flange 30, and an outwardly extending lower edge 32, as seen in FIG. 6.

Lip 28 of cover 14 provides a stop surface for engaging the top surface 16 of base 12 and thereby limiting downward movement of cover 14 with respect to base 12. Along the lower edge 32 of cover 14, are a plurality of indentations 34, at least at the corners of the cover, which allows cover 14 to snap fit over the lip 23 of base 12, and thereby secure the cover to the base. Dimples 35 may be provided on flange 30 of cover 14 to provide increased frictional engagement with lip 23 of base 12. While the drawings show lip 23 extending continuously around base 12, it is understood that individual spaced apart projections could also be provided for overlapping engagement by the indentations 34 on cover 14.

In use, syringe 36 are placed in the respective ports 22 of base 12 and cover 14 is placed over the syringes and snap fit onto the lip 23 of base 12. As seen in FIG. 5, ports 22 are sufficiently deep to receive the barrel 38 of syringe 36, but the ports do not extend clear through the base. As shown in the drawings, syringe 36 also includes a hollow plunger 40 with a housing 42 for the needle (not shown) being received within the plunger. It is understood that ports 22 can be of any shape and configuration to receive other styles of syringes, without departing from the scope of the present invention. FIG. 5 also illustrates syringe 36 as being pre-filled with a medicinal fluid 44.

Base 12 is made of an insulative material, such as styrofoam or the like, which protects the medicinal fluid 44 from temperature extremes. Also, cover 14 sealingly engages base 12 so as to provide an air-tight enclosure for the syringes. Such air-tightness provides for the insulation for the fluid. Preferably, cover 12 is transparent so that identifying indicia on the syringes can be easily viewed. Also, since the bottom of the base and the top of the cover are flat, multiple containers 10 can be stacked one upon another for shipping and storage.

From the foregoing description, it can be seen that the present invention accomplishes at least all of the stated objectives.

What is claimed is:

1. A container for storing and shipping syringes, each syringe including a barrel for holding fluid to be injected, a needle attachable to the barrel, and a plunger for ejecting the fluid froom the barrel and through the needle, the container comprising;

a base integrally formed from insulative material, having a top, a bottom, and interconnected sidewalls, and having a plurality of ports extending downwardly from the top without extending through the base, each port being adapted to receive a syringe;

a cover having a closed top, interconnected corrugated side walls terminating in a lower edge, and an open bottom so as to fit over the syringes, and having lip means for engaging the top of the base to limit downward movement of the cover with respect to the base;

means for snap fitting the cover to the base, including outwardly projecting lip means on the sidewall of the base and indentation means on the lower edge of the cover, the sidewalls of the cover being resilient such that said indentation means can pass over the lip means to overlapping and retentatively engage the lip means so as to hold said cover in position on said base; and the ports in the base being formed in rows, with the ports in each row being interconnected so as to define an elongated furrow for receiving a plurality of syringes.

2. The container of claim 1 wherein the top of the cover is flat and the bottom of the base is flat so that multiple containers are stackable one upon another.

3. The container of claim 1 wherein the cover sealingly engages the base to provide an air-tight enclosure for the syringes.

4. The container of claim 1 wherein the cover is transparent.

5. The container of claim 1 wherein the cover includes dimples adjacent the lower edge to provide frictional engagement with the base.

6. A container for storing and shipping syringes, each syringe including a barrel for holding fluid to be injected, a needle attachable to the barrel, and a plunger for ejecting the fluid from the barrel and through the needle, the container comprising;

a base having a top, a bottom, and interconnected sidewalls, and having an elongated furrow extending downwardly from the top, adapted to receive a plurality of syringes;

a cover having a closed top, interconnected sidewalls terminating in a lower edge, and an open bottom so as to fit over the syringes; and means for securing the cover to the base.

7. The container of claim 6 wherein the furrow has opposite sidewalls with projections extending towards one another from each sidewall so as to define a plurality of ports, each of which is adapted to receive a syringe.

8. The container of claim 6 wherein the means for securing the cover to the base includes outwardly projecting lip means on the sidewalls of the base and indentation means on the lower edge of the cover, the sidewalls of the cover being resilient such that said indentation means can pass over the lip means to overlapping and retentively engage the lip means so as to hold said cover in position on said base.

9. The container of claim 6 wherein the sidewalls of the cover are corrugated to provide strength to the cover.

10. The container of claim 6 wherein the cover includes lip means for engaging the top of the base to limit downward movement of the cover with respect to the base.

11. The container of claim 6 wherein the base is made of insulative material to protect fluid in the syringes from temperature extremes.

12. The container of claim 6 wherein the top of the cover is flat and the bottom of the base is flat so that multiple containers are stackable one upon another.

13. The container of claim 6 wherein the cover sealingly engages the base to provide an air-tight enclosure for the syringes.

14. The container of claim 6 wherein the furrow extends partially into the base without extending through the base.

15. The container of claim 6 wherein the cover is transparent.

16. The container of claim 6 wherein the cover includes dimples adjacent the lower edge to provide frictional engagement with the base.

* * * * *